US012573032B2

(12) United States Patent
Diaz et al.

(10) Patent No.: US 12,573,032 B2
(45) Date of Patent: Mar. 10, 2026

(54) SYSTEM AND METHODS OF PREDICTING PARKINSON'S DISEASE BASED ON RETINAL IMAGES USING MACHINE LEARNING

(71) Applicant: University of Florida Research Foundation, Inc., Gainesville, FL (US)

(72) Inventors: Maximillian Diaz, Gainesville, FL (US); Ruogu Fang, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 243 days.

(21) Appl. No.: 18/038,517

(22) PCT Filed: Nov. 30, 2021

(86) PCT No.: PCT/US2021/061182
§ 371 (c)(1),
(2) Date: May 24, 2023

(87) PCT Pub. No.: WO2022/115777
PCT Pub. Date: Jun. 2, 2022

(65) Prior Publication Data
US 2024/0020830 A1      Jan. 18, 2024

Related U.S. Application Data

(60) Provisional application No. 63/119,039, filed on Nov. 30, 2020.

(51) Int. Cl.
*G06T 7/00*      (2017.01)
*G16H 30/40*      (2018.01)
*G16H 50/20*      (2018.01)

(52) U.S. Cl.
CPC .......... *G06T 7/0012* (2013.01); *G16H 30/40* (2018.01); *G16H 50/20* (2018.01);
(Continued)

(58) Field of Classification Search
USPC ...... 128/920–925; 382/100–225; 704/1–275; 706/1–62, 900–903
See application file for complete search history.

(56) References Cited

U.S. PATENT DOCUMENTS 11,013,452 B1 *   5/2021   Song ................... A61B 5/7275
2021/0076936 A1 *  3/2021   Agichtein ............. A61B 5/168
(Continued)

FOREIGN PATENT DOCUMENTS

| WO | 2018069768 A2 | 4/2018 |
| WO | 2020188471 A1 | 9/2020 |

OTHER PUBLICATIONS

Sylvestre Jean Philippe; Method and System for Identifying Subjects Who Are Potentially Impacted by a Medical Condition; 2023 (Year: 2023).*
(Continued)

*Primary Examiner* — Marcellus J Augustin
(74) *Attorney, Agent, or Firm* — Thomas I Horstemeyer, LLP

(57) ABSTRACT

Various examples are provided related to machine learning for Parkinson's Disease diagnosis, systems, and methods. In one example, a method for identification of onset or presence of Parkinson's disease (PD) includes receiving a retinal image that has been acquired by an image acquisition system; processing the acquired retinal image using one or more trained machine learning models to classify one or more retinal features contained in the acquired retinal image; and predicting, by the processing circuitry, whether the retinal image is indicative of an onset or presence of PD in
(Continued)

the human subject based on the classification. A machine learning system can perform trained machine learning. Machine learning models can trained on stored retinal images obtained from a group of subjects who have previously been diagnosed as having PD and a group of subjects who have not previously been diagnosed as having PD.

13 Claims, 3 Drawing Sheets

(52) U.S. Cl.
  CPC .............. *G06T 2207/20081* (2013.01); *G06T 2207/20084* (2013.01); *G06T 2207/30041* (2013.01)

(56) References Cited

U.S. PATENT DOCUMENTS

| | | | |
|---|---|---|---|
| 2022/0237786 A1* | 7/2022 | Pernia | A61P 25/00 |
| 2022/0293277 A1* | 9/2022 | Mande | G16B 30/00 |
| 2023/0050186 A1* | 2/2023 | Rotenstreich | A61B 5/7267 |

OTHER PUBLICATIONS

International Search Report for PCT/US21/61182 mailed Jul. 1, 2022.
Wingate, et al., "A unlfied deep learning approach for prediction of parkinson's disease", IET Image Processing, 14(10) Nov. 25, 2019.

* cited by examiner

300

MACHINE LEARNING MODELS
320

PROCESSOR
310

330

DISPLAY
DEVICE
311

PRINTER
312

IMAGE
ACQUISITION
SYSTEM
340

SYSTEM AND METHODS OF PREDICTING PARKINSON'S DISEASE BASED ON RETINAL IMAGES USING MACHINE LEARNING

CROSS REFERENCE TO RELATED APPLICATIONS

This application is the 35 U.S.C. § 371 national stage application of PCT Application No. PCT/US2021/061182, filed Nov. 30, 2021, which claims priority to, and the benefit of, U.S. provisional application entitled "Machine Learning for Predicting Parkinson's Disease Based On Retinal Fundus Images", having Ser. No. 63/119,039, filed Nov. 30, 2020, both of which are hereby incorporated by reference herein in their entireties.

BACKGROUND

Parkinson's Disease (PD) is the second most common form of neural degeneration and defined by the decay of dopaminergic cells in the substantia nigra. The current standard for diagnosing PD occurs once 80% of dopaminergic cells have decayed. The degradation of these cells has been shown to create thinning of the retina walls and retina microvasculature.

SUMMARY

Aspects of the present disclosure are related to machine learning for Parkinson's Disease diagnosis, systems, and methods thereof.

In one aspect, among others, a machine learning system can classify retinal features and predict, based on the classified retinal features, an onset or presence of Parkinson's disease (PD) in a human subject. The machine learning system can comprise a processor configured to perform trained machine learning, wherein one or more trained machine learning models have been trained on stored retinal images obtained from at least a first group of human subjects who have previously been diagnosed as having PD and at least a first group of human subjects who have not previously been diagnosed as having PD; and a memory device in communication with the processor, the memory device storing computer instructions comprising the one or more trained machine learning models for execution by the processor. The one or more trained machine learning models can perform a process comprising receiving a retinal image that has been acquired by an image acquisition system; processing the acquired retinal image to classify one or more retinal features contained in the acquired retinal image; and predicting, based on the classification, whether the retinal image is indicative of an onset or presence of PD in the human subject. The retinal images can comprise retinal fundus images.

In one or more aspects, the one or more trained machine learning models can be configured in a pipeline architecture comprising a trained vessel map generator machine learning model in a first stage of the pipeline architecture and a trained PD classifier machine learning model in a second stage of the pipeline architecture that follows the first stage. During training of the PD classifier machine learning model, the trained vessel map generator machine learning model can generate respective vessel maps for each respective retinal image inputted to the first stage and can output the vessel maps to the second stage. During training of the PD classifier machine learning model, the vessel maps outputted to the first stage can be used to train the PD classifier model. After the PD classifier machine learning model has been trained to classify retinal images, a retinal image obtained from a patient can be processed by the trained vessel map generator machine learning model to produce a respective vessel map that is outputted to the second stage. The respective vessel map can be processed by the trained PD classifier machine learning model to predict, based on the classification, whether the retinal image is indicative of an onset or presence of PD in the human subject.

In another aspect, a method for identification of onset or presence of Parkinson's disease (PD) comprises receiving, by processing circuitry, a retinal image that has been acquired by an image acquisition system; processing, by the processing circuitry, the acquired retinal image using one or more trained machine learning models to classify one or more retinal features contained in the acquired retinal image; and predicting, by the processing circuitry, whether the retinal image is indicative of an onset or presence of PD in the human subject based on the classification. In one or more aspects, the one or more trained machine learning models can be trained on stored retinal images obtained from at least a first group of human subjects who have previously been diagnosed as having PD and at least a first group of human subjects who have not previously been diagnosed as having PD. The retinal image can be a retinal fundus image or can be generated from an optical coherence tomography (OCT) image.

In various aspects, the one or more trained machine learning models can be configured in a pipeline architecture comprising a trained vessel map generator machine learning model in a first stage of the pipeline architecture and a trained PD classifier machine learning model in a second stage of the pipeline architecture that follows the first stage. The method can comprise training a PD classifier machine learning model to generate the trained PD classifier machine learning model. During training of the PD classifier machine learning model, the trained vessel map generator machine learning model can generate respective vessel maps for each respective retinal image inputted to the first stage and outputs the vessel maps to the second stage. During training of the PD classifier machine learning model, the vessel maps outputted to the first stage can be used to train the PD classifier model. The method can comprise processing a retinal image obtained from a patient by the trained vessel map generator machine learning model to produce a respective vessel map that is outputted to the second stage; and processing the respective vessel map by the trained PD classifier machine learning model to predict, based on the classification, whether the retinal image is indicative of an onset or presence of PD in the human subject.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
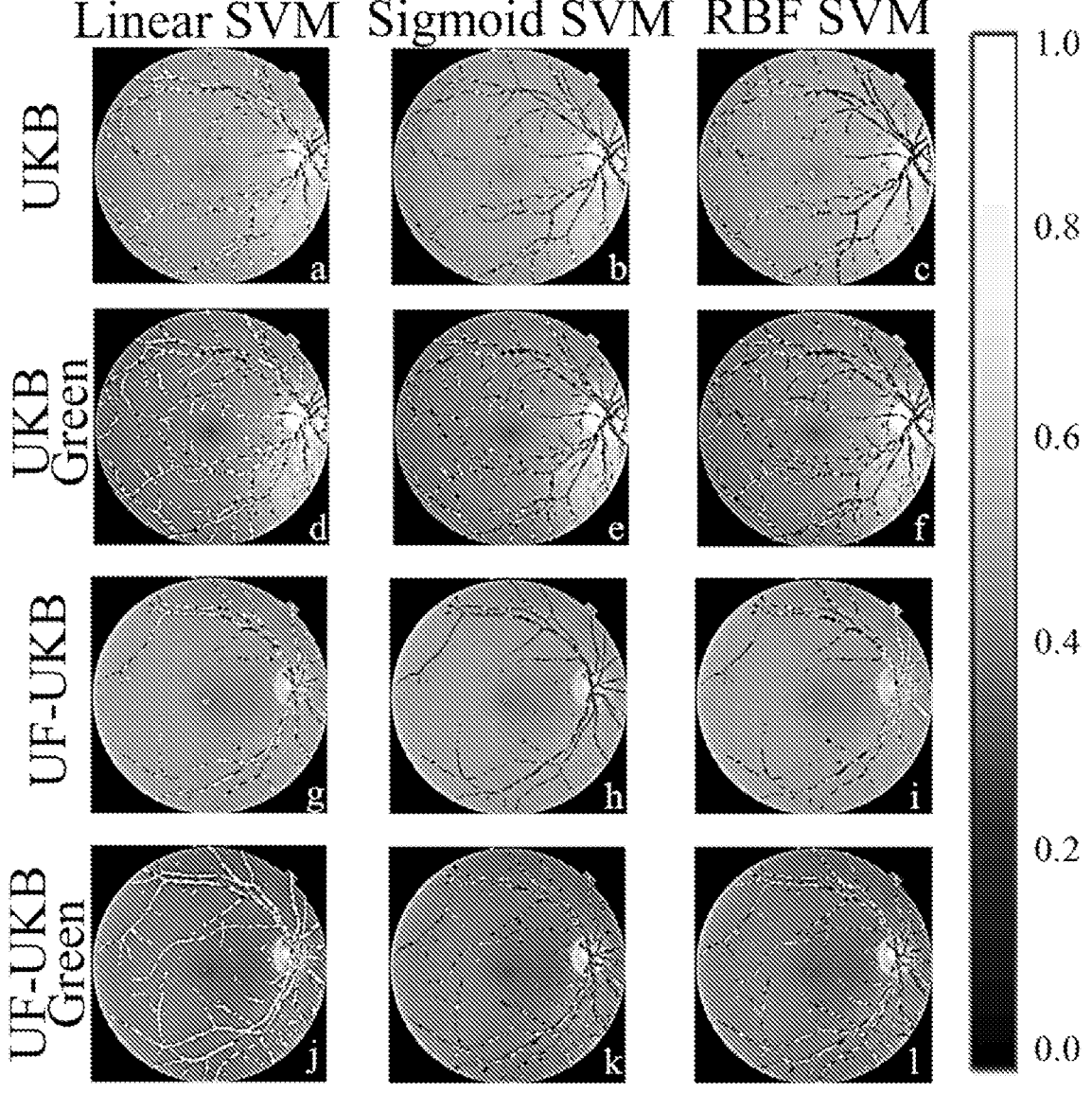
FIG. 1 includes examples of saliency maps illustrating the regions of importance determined by an SVM, in accordance with various embodiments of the present disclosure.

Disclosed herein are various examples related to machine learning for Parkinson's Disease diagnosis, systems, and methods thereof. This disclosure presents machine learning techniques to provide Parkinson's Disease (PD) diagnosis using non-invasive eye images such as, e.g., fundus images and optical coherence tomography (OCT) images. The feasibility of utilizing eye images as a method for diagnosing PD, opposed to the current method of using motor symptoms, is illustrated. The methodology can diagnosis Parkinson's Disease using eye blood vessels taken from retinal images. The eye blood vessels can be segmented using a convolutional neural network, and then used to diagnosis Parkinson's patients using support vector machine classifiers. Reference will now be made in detail to the description of the embodiments as illustrated in the drawings, wherein like reference numbers indicate like parts throughout the several views.

PD is pathologically defined by the decay of dopaminergic neurons in the substantia nigra, the region of the brain responsible for dopamine production and movement. In addition, PD is associated with the presence of Lewy body proteins and Lewy neurite threads in neurons outside of the substantia nigra. The current clinical gold standard for diagnosing PD is the presence of motor symptoms, which primarily occur once a patient has lost approximately 80% of dopaminergic cells. Therefore, research has begun focusing on nonmotor symptoms for earlier PD diagnosis. Such symptoms include cardiac arrhythmias, sleep disorders, constipation, vocals, and gait. This disclosure explores a nonmotor method for diagnosing PD that can be used to develop a new clinical standard that diagnoses earlier stages of PD.

Machine learning can be utilized in the identification of PD due to its ability to analyze complex data structures. For example, machine learning can be used to diagnose patients with PD from control subjects (CN) using parameters obtained from subjects' gaits. Previous work has combined force sensors, accelerometers, and images as inputs to support vector machine (SVM), logical analysis of data (LAD), and shallow convolution neural networks (CNN). Furthermore, machine learning can also be used with nonmotor symptoms to diagnosis PD.

The retina provides researchers with the unique opportunity to study neurodegeneration without directly analyzing the brain. The optic nerves are two of the 12 major cranial nerves and can be viewed using standard photography or imaging. Research into PD has shown simultaneous decreases in dopaminergic cells present in the substantia nigra and the retinas. The resulting lack of dopamine in the retinas leads to thinning of several retina layers by 15 to 20% which can be observed with OCT imaging techniques. In addition to thinning of the retina layers, it has been shown that there is a statistical difference ($P<0.01$) between a decreased microvascular network and the progression of PD using spectral-domain optical coherence tomography (SD-OCT).

The current disclosure demonstrates the eye's potential to provide insight into physiological changes occurring within the brain by exploring the ability to detect Parkinson's disease from basic eye images (e.g., fundus eye images). While OCT imaging can provide three dimensional structures of the eye, fundus eye images provide a more clinically relevant diagnosis tool due to its increased portability and affordability since it is simply a photograph of the back of the eye. If OCT imaging is available, similar information can be extracted from a OCT image through processing. The current disclosure applies machine learning algorithms to retina vascular structures to demonstrate that eye data can be leveraged as a potential means for early PD diagnosis.

A machine learning system and method are disclosed herein that classify retinal features and predict, based on the classified retinal features, the onset or presence of Parkinson's disease in a human subject. The system can comprise a processor configured to perform one or more machine learning models and a memory device in communication with the processor. The machine learning model(s) can be trained to process retinal fundus images acquired by an image acquisition system to classify retinal features contained in the images and to predict, based on the classified retinal features, whether the images are indicative of the presence or onset of Parkinson's disease.

Machine learning model(s) can be trained to classify retinal features contained in retinal images (e.g., retinal fundus images) and to predict, based on the classification, the onset or presence of PD in a human subject. Once trained, the machine learning model(s) can analyze retinal images captured by an image acquisition system to identify and classify retinal features contained in the images. Based on the classification of the retinal features, the machine learning model(s) can predict the onset or presence of PD in the human subject.

The machine learning can be implemented using datasets comprising retinal fundus images. While the machine learning is disclosed with respect to specific databases, other databases or datasets may also be used. Two age and gender matched datasets where constructed using data from the UK Biobank (UKB) and data collected at the University of Florida (UF). The first dataset consisted of 476 fundus eye images, 238 CN and 238 PD, sourced entirely from the UKB database. The second dataset, UF-UKB, consisted of 100 images, 28 CN and 72 PD, collected at UF and 44 CN images from UKB. A second set of datasets, UKB-Green and UF-UKB-Green, was created using the green color channels to improve vessel segmentation. Vessel segmentation was performed using U-Net segmentation network. The vessel maps served as inputs to SVM classifying networks. Saliency maps were created to assess areas of interest for the networks.

UKB Dataset for SVM. Machine learning classifiers generalize to unseen data better when trained on a large robust dataset. The current study collected data from UK Biobank (https://www.ukbiobank.ac.uk/). This database was chosen because it is not disease specific, which means that it provides multiple data fields for all subjects and is not limited to a specific disease. This allows the unique opportunity to acquire a large volume of fundus eye images from patients with PD. UK Biobank (UKB) included data from 2,268 subjects with PD at the time of this study. The diagnosis for PD was obtained from ICD-10 codes collected from patient medical and death records. UK Biobank's total fundus images included 87,569 left fundus images and 88,255 right fundus images from PD, control normal (CN), and other disease study participants.

A matching process identified fundus images that correlated to patients with a diagnosis of PD. In total, this corresponded to 585 images from 296 patients with PD with potentially 291 left fundus images and 294 right fundus images. However, these images were originally collected as guide images for optical coherence tomography (OCT) and hence vary widely in image quality. Therefore, this study integrated a stage for quality screening to mitigate this variance. During this process, images were evaluated by a trained researcher and removed due to the presence of comorbidities, overexposure, underexposure, or artifacts. The screening process resulted in 142 left fundus images and 123 right fundus images from a total of 168 subjects with PD. To limit potential age bias, the PD images were then paired with CN images of matching gender and age at the time of image capture. The UKB database offers fundus images from 61,281 CN subjects, with 61,281 left fundus images and 61,464 right fundus images.

Prior to quality screening, potential CN images were age and gender matched to the acceptable PD images. This resulted in a total of 1,438 potential fundus images, including 624 and 814 from the right and left eye, respectively. The CN images then underwent the same quality screening, during which 119 right fundus images and 124 left fundus images from 185 subjects were found to be acceptable quality. Five of the left fundus images were then randomly removed to allow for a balance between the number of right and left eyes. The unmatched PD images were then removed from the dataset. Therefore, the final dataset consisted of 476 fundus eye images with 238 PD images and 238 CN images from 154 subjects with PD and 184 CN subjects, respectively (FIG. 2). The average age for the dataset was 60.97 years old with a standard deviation of 6.35 years. The resulting dataset is referred to as the UKB dataset and is summarized in Table 1.

TABLE 1

| UKB Dataset Demographics | |
| --- | --- |
| Demographic | Value |
| Mean Age | 60.9 |
| Standard Deviation of Age | 6.4 |
| CN Images | 238 |
| PD Images | 238 |
| Total images | 476 |

Clinical UF-UKB dataset. One aspect of the present study was to assess the viability of a machine learning classifier to aid in diagnosis in a clinical setting. Therefore, fundus images were collected from patients with PD at the University of Florida (UF), Fixel Neurological Institute, Movement disorders center. The University of Florida institutional review board (IRB) approved this study's experimental procedures prior to data collection from patients. Trained student researchers obtained fundus images from patients with clinically diagnosed PD and their spouses using a Remidio NM Fundus on Phone Camera (NMFOP) (Remidio Fundus on Phone [FOP]; Remidio Innovative Solutions Pvt. Ltd., Bengaluru, India). The NMFOP is a specialized lens that attaches to a smartphone; hence, it facilitates increased portability and reduced equipment costs as compared to traditional fundus imaging systems.

Prior to further processing, the study team subjected the UF dataset to the same quality screening processes as those performed on UKB dataset. This step reduces natural variations in image quality that can occur due to patient comorbidities and variance in image capture techniques. The screening resulting in an initial UF dataset of 72 PD images and 28 CN images. The low number of CN images resulted from age and gender matching to PD images. This process can mitigate age bias on the experiments; however, the study team sought to increase the size of the CN images in this dataset (as opposed to decreasing the number of PD images). Hence, additional CN images were obtained from the UK Biobank Database that matched the age and gender of the remaining PD images. Therefore, the final dataset consisted of 144 fundus eye images with 72 PD images and 72 CN images. Of these, the study obtained 100 images at UF and 44 images from UKB. The mean age for the dataset was 66 with a standard deviation of 9 years. The resulting dataset is referred to as the UF-UKB dataset and is summarized in Table 2.

TABLE 2

| UF-UKB Dataset Demographics | | | |
| --- | --- | --- | --- |
| Demographic | UF | UKB | Total |
| Mean Age | 37.6 | 66.3 | 44 |
| Standard Deviation of Age | 23.5 | 9.6 | 22.5 |
| CN Images | 28 | 44 | 72 |
| PD Images | 72 | 0 | 72 |
| Total Images | 100 | 44 | 144 |

Green Channel for improved segmentation. Initial segmentation experiments exhibited difficulty in accurately segmenting all the vessels in an image. The network had difficulty segmenting the smaller vessels of the images. FIG. 1 shows examples of saliency maps illustrating the regions of importance determined by an SVM. Hence, grayscale images were created from green color channels to remedy this shortcoming and improve vessel segmentation. Use of only the green color channel provided improved vessel segmentation. This method created two new datasets, UKB-Green and UF-UKB-Green, in which the original RGB images were converted to grayscale using the values taken from the green color channel.

Figures 2A, 2B:
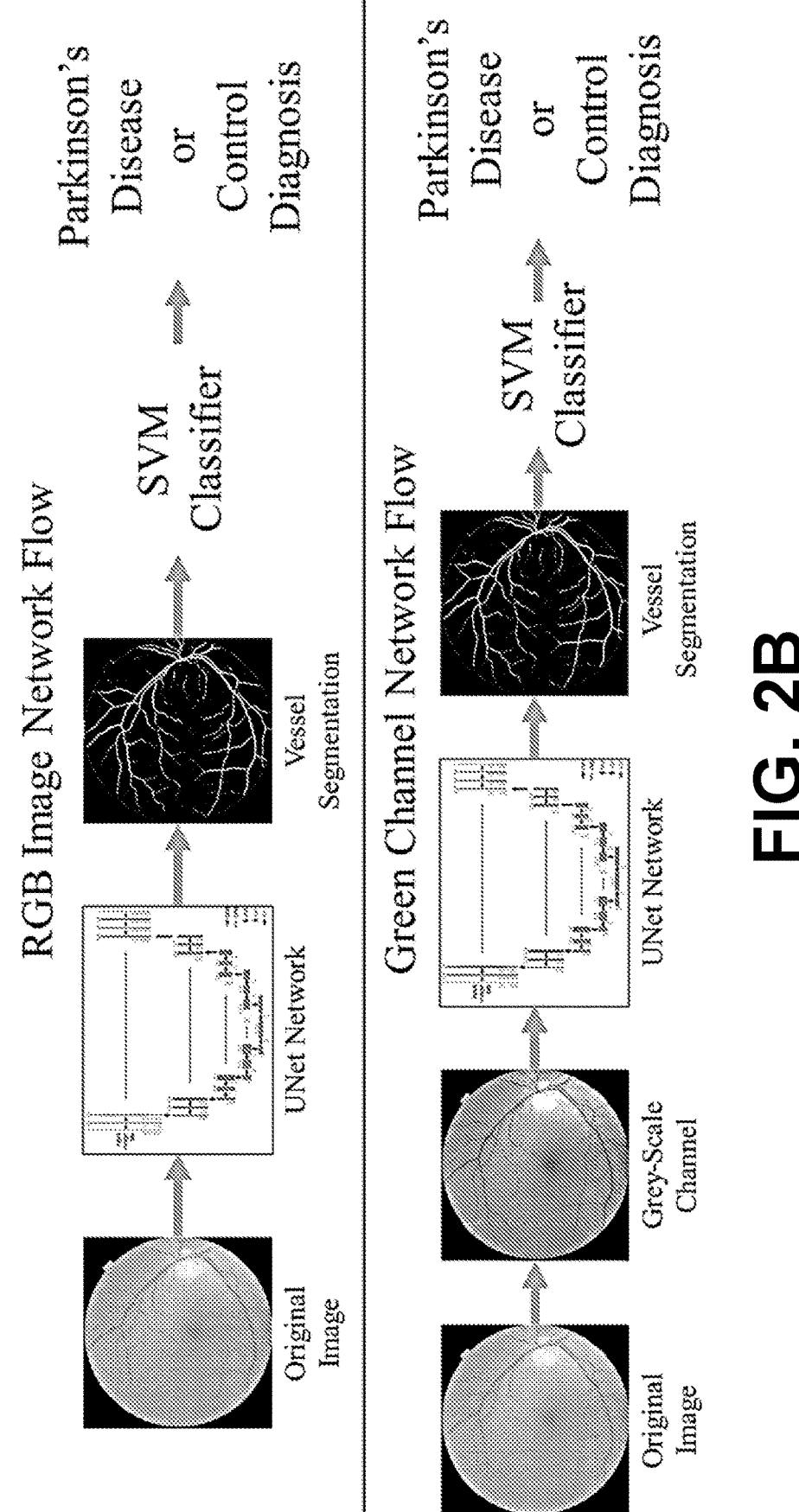
FIGS. 2A and 2B illustrate examples of machine learning, in accordance with various embodiments of the present disclosure.

Machine learning. Examples of the machine learning are illustrated in FIGS. 2A and 2B. In FIG. 2A, blood vessels can be selected from the retinal image(s) (e.g., one or more fundus image) by a machine learning network (e.g., a Unet network) which was trained to select blood vessels in the eye of a subject. The vessels can then be fed into an SVM classifier to determine if the subject has PD. In FIG. 2B, a grey scale image is created from the retinal image and then the vessels can be selected by the same machine learning network to improve the selection of the blood vessels. Other retinal images such as, e.g., fundus vasculature images generated from OCT images can also be used for the determination of PD.

Image preprocessing. All images were cropped to remove excess black background and maintain the entire fundus eye image. The images collected at UF were cropped to 2100 pixels by 2100 pixels; the images obtained from UKB were cropped to 1369 pixels by 1369 pixels. The cropping size was determined based on the size of the original image.

Vessel Segmentation. The vessel segmentation network used the U-Net architecture as its basis. This network was chosen since it was originally developed for the segmentation of biomedical images. The network was then trained using the public Digital Retinal Images for Vessel Extraction (DRIVE) database. The DRIVE dataset consists of 40 retina images with masks provided for vessel segmentation. The developed network achieved an accuracy of 0.89 on testing data from the DRIVE database. The resulting architecture performed automated vessel segmentation on each of the unique four datasets as the final preprocessing step.

SVM classifier experiments. The datasets were randomly split to use 80% of the data for the development of the SVM classifiers and the remaining 20% for testing. All retinal images from the same subject only appeared in either the training or test set; they were not in both to present data leakage. The segmented images were all scaled to 210 by 210 color images to allow for constant size between images from UF and UKB. The classifier imputed the flattened vector form of these resized images. The classifiers were then trained in Python 3.6.9 using fivefold cross validation. These experiments tested three different SVM classifiers per dataset (linear, sigmoid, or radial basis function (RBF) kernel) to establish the best classifier kernels.

The top performing SVM network for the UKB and UKB-Green datasets were the sigmoid SVM networks which achieved accuracies of 0.698 and 0.719 respectively. Meanwhile the top performing networks for the UF-UKB and UF-UKB-Green datasets where the linear SVM networks which achieved accuracies of 0.821 and 0.857 respectively. The saliency maps indicate that the different networks focused on different vessel structures with the most successful networks focusing more on smaller vessels.

Saliency Maps for key vessel visualization via an occlusion test. Saliency maps visualized regions of interest in the vessel segmentation. An occlusion technique, which is an ad-hoc explanation approach by removing a small region (set as black) in the input image and evaluate the change in prediction confidence as a measure of the importance of the region removed, generated these maps. This procedure entails a 1×1 moving window that progressively set each pixel value of the segmented image to zero. Each resulting image was then feed through the trained SVM classifier to calculate the importance of that pixel. Prediction confidences were then stitched together and normalized to develop a saliency map that showed the relative importance of each pixel.

Machine learning system. A machine learning system can classify retinal features and predict, based on the classified retinal features, the onset or presence of Parkinson's disease in a human subject. The system can comprise a processor configured to perform one or more machine learning models and a memory device in communication with the processor. The machine learning model(s) can be trained to process retinal fundus images acquired by an image acquisition system to classify retinal features contained in the images and to predict, based on the classified retinal features, whether the images are indicative of the presence or onset of Parkinson's disease. An example of a machine learning system is shown in FIG. 3.

Figure 3:
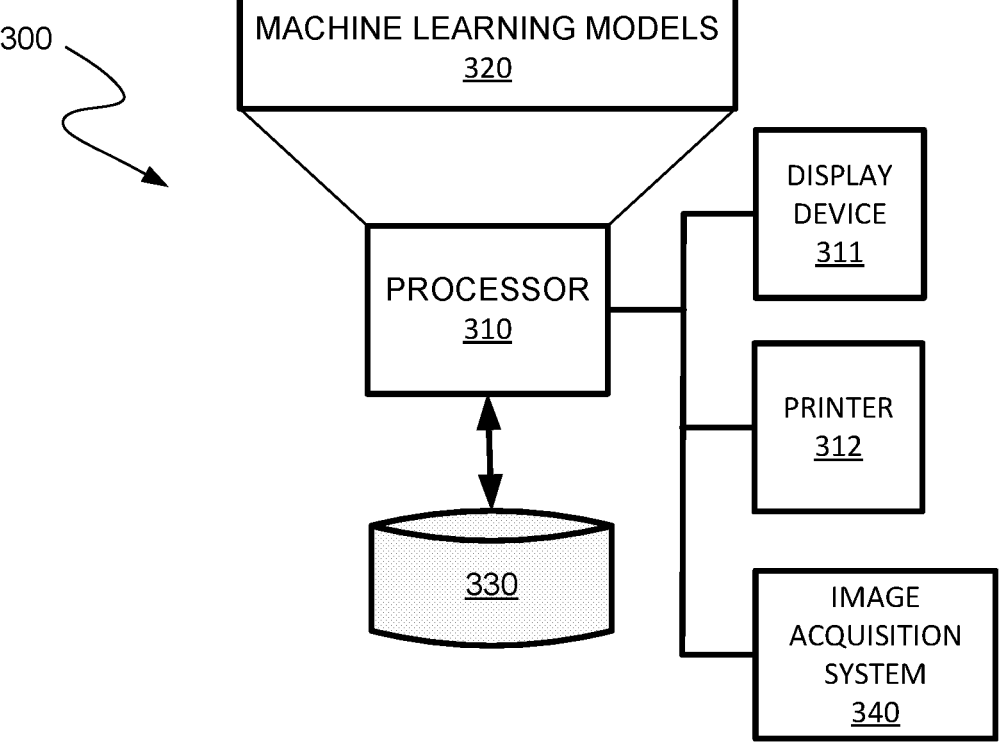
FIG. 3 is a block diagram illustrating an example of a machine learning system, in accordance with various embodiments of the present disclosure.

In the example of FIG. 3, the machine learning system 300 illustrates a representative embodiment for predicting Parkinson's disease in a human subject. Processing circuitry of the system 300 including a processor 310 can be configured to perform one or more machine learning models 320, which can be implemented in hardware, software, firmware, or a combination thereof. A memory device 330 of the system can store computer instructions comprising the model(s) 320. The memory device 330 can also store a database of retinal images (e.g., fundus images, OCT images, and/or their derivatives) that may be used by the machine learning model(s) 320. In some embodiments, the database of retinal images may be stored in a storage system that is external to the system 300 and accessible by the processor 310. The system 300 may optionally include a display device 311, a printer 312 and an image acquisition system 313. In some embodiments of the system 300, the image acquisition system 313 acquires fundus images for processing by the machine learning model(s) 320. In other embodiments of the system 300, the fundus images, OCT images or other appropriate retinal images are provided to the system 300. Therefore, the image acquisition system 313 can be part of the system 300 or external to the system 300. The components 310, 311, 312, 313 and 330 of the system 300 are in communication with one another over a network or bus 315. The components 310, 311, 312, 313 and 330 can be co-located or they can be distributed over one or more networks.

The machine learning model(s) 320 can be trained to classify retinal features contained in retinal images and to predict, based on the classification, the onset or presence of PD in a human subject. Once trained, the machine learning model(s) 320 can analyze retinal fundus images captured by the image acquisition system 313 to identify and classify retinal features contained in the images. Based on the classification of the retinal features, the machine learning model(s) 320 predicts the onset or presence of PD in the human subject.

The flow charts of FIGS. 2A and 2B illustrate the architecture, functionality, and operation of a possible implementation of the machine learning models. In this regard, each block represents a module, segment, or portion of code, which comprises one or more executable instructions for implementing the specified logical function(s). It should also be noted that in some alternative implementations, the functions noted in the blocks may occur out of the order noted in FIG. 2A or 2B. For example, two blocks shown in succession may in fact be executed substantially concurrently or the blocks may sometimes be executed in the reverse order, depending upon the functionality involved, as will be further clarified hereinbelow.

The machine learning models, which comprise an ordered listing of executable instructions for implementing logical functions, can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM or Flash memory) (electronic), an optical fiber (optical), and a portable compact disc read-only memory (CDROM) (optical). In addition, the scope of the certain embodiments of the present disclosure includes embodying the functionality of the preferred embodiments of the present disclosure in logic embodied in hardware or software-configured mediums.

Results

SVM classification on large datasets. Table 3 shows the resulting classification accuracy when the classification process was applied to the original UKB dataset. The linear and sigmoid SVM each resulted in a classification accuracy of 0.698, compared to the RBF-Kernel SVM which only obtained an accuracy of 0.635. However, there is no clear best classifier when the performances are judged by specific and sensitivity. The linear SVM classifier achieved the lowest sensitivity of 0.625 and the highest specificity of 0.771. The sigmoid SVM achieved highest sensitivity of 0.75 and the median specificity of 0.646. In contrast, the RBF-kernel SVM achieved the median sensitivity of 0.729 and the lowest specificity of 0.541.

TABLE 3

Performances of networks trained on UKB and UKB-Green

| Method | Accuracy(%) | Sensitivity(%) | Specificity(%) |
| --- | --- | --- | --- |
| UKB Linear | .698 | .625 | .771 |
| UKB Sigmoid | .698 | .750 | .646 |
| UKB RBF | .635 | .729 | .541 |
| UKB-Green Linear | .688 | .604 | .771 |
| UKB-Green Sigmoid | .719 | .792 | .646 |
| UKB-Green RBF | .656 | .680 | .625 |

SVM's viability in a clinical setting. The SVM classifiers developed on the UF-UKB datasets successfully classified PD from CN based on clinical data (Table 4). The linear SVM classifier provided the best performance with accuracy, sensitivity, and specificity of 0.821, 0.786, and 0.858, respectively. The sigmoid SVM and RBF-kernel SVM had the same performance of 0.786 for accuracy, sensitivity, and specificity. The sigmoid SVM classifier had the highest area under the curve (AUC), which traditionally means that it was the best performing classifier; however, the researchers believed that a classifier developed for clinical applications was better evaluated using accuracy, sensitivity, and specificity. This is based on the idea that the process seeks to provide the accurate diagnosis for patients in a clinical setting, and the metrics that best identify this performance are the accuracy, sensitivity, and specificity.

TABLE 4

Network performances from UF-UKB and UF-UKB-Green

| Method | Accuracy (%) | Sensitivity(%) | Specificity(%) |
| --- | --- | --- | --- |
| UF-UKB Linear | .821 | .786 | .857 |
| UF-UKB Sigmoid | .786 | .786 | .786 |
| UF-UKB RBF | .786 | .786 | .786 |
| UF-UKB-Green Linear | .857 | .786 | .929 |
| UF-UKB-Green Sigmoid | .821 | .786 | .857 |
| UF-UKB-Green RBF | .821 | .786 | .857 |

Green color channel for improved performance. Extracting the green color channel improved the vessel segmentation; however, the resulting vessel segmentations had varying effects on the performance of the SVM classifiers when applied to the UKB-Green dataset. The sigmoid SVM increase accuracy to 0.719, and sensitivity to 0.792; it maintained the same specificity of 0.646. However, the linear SVM decreased its accuracy to 0.688, and sensitivity to 0.604; specificity remained unchanged at 0.771. Furthermore, the RBF-kernel SVM increased its accuracy to 0.656 and specificity to 0.625; sensitivity decreased to 0.688. The green color channel images improved accuracy and specificity for all three classifiers with the UF-UKB-Green dataset. The linear SVM performed the best with an improved accuracy and specificity of 0.857 and 0.929, respectively.

The sigmoid SVM and RBF-kernel SVM again performed equally with improved accuracy and specificity of 0.821 and 0.857, respectively. The green dataset likely improved performance across all the classifiers for the UF-UKB-Green dataset due to the improved vessel segmentation. This allowed more information to pass to the classifier. Hence, the machine learning algorithm identified more potential biomarkers, rather than it classifying results based on the larger vessels alone. This also explains why the improvements where limited in the UKB-Green dataset as the selected images and their segmentations were of a higher quality compared to the UF-UKB dataset prior to using green color channels.

Saliency Maps for network visualization. The evaluation of the maps indicated that the linear classifiers emphasized structures throughout the entire vessel structure. They consistently highlighted the image's smallest vessels the most, which is consistent with findings from spectral-domain OCT. In contrast, the worst performing classifiers, RBF-kernel SVM, emphasized vessels around the optic nerve and ignored smaller vessels. The visualizations show that changes in the smaller vasculature can provide a biomarker for classifying PD. Weight maps were not generated since the RBF and sigmoid kernel types cannot harness this method. Thus, saliency maps provide better cross comparison between the three networks when identifying regions of importance. The saliency map places importance based on prediction confidence, whereas weight maps signify importance by model's weight parameters. This means that comparing the two methods would harness regions of interested generated from different metrics. Hence, the cross examination would be weak.

Discussion. Utilizing retina fundus images as input modalities to a Parkinson's disease SVM classifier illustrated three main findings. First, SVM classifiers can classify patients with PD from CN using only retina fundus images with reasonable accuracy. This finding supports that differences exist in the retina vasculature of patients with PD; however, the present study's results also show that machine learning classifiers can observe these differences using basic fundus or other images. Second, the entire classification process can be automated for increased repeatability and clinical efficiency. The current approach provides a novel procedure by eliminating the need for manual segmentation, instead providing an automated system that performs segmentation and classification regression. This approach may be better suited for a clinical setting because it allows for physicians to dedicate more time to patient care. Third, the machine learning classification performances are reliant on the method of vessel segmentation. Since classifiers' performances varied with the method of vessel segmentation, further work must identify how this segmentation approach affects the classifier decision.

In addition to the findings, a longitudinal program for the study of PD progression can incorporate the collection of retina images to develop a dataset for use of retina vasculature for early diagnosis of PD. This dataset can aid researchers in further developing methods for prediction and early diagnosis of PD. Second, a larger clinical dataset can include multiple clinics to allow for a better gauge of the ease and accuracy of clinical integration. Finally, the saliency maps identify regions of interest that the classifiers use to identify PD from CN, which may indicate biomarkers that the machine learning classifier is identifying. Using a larger dataset to identify a correlation between regions of interest may narrow down the PD biomarkers present in the eye.

In conclusion, the proposed machine learning framework uses U-Net to automatically segment vessels and linear kernel SVM to diagnose PD based on vascular structures. This methodology provides a viable alternative to tremor-based diagnosis and illustrates the potential of using the retina as a potential modality for neurological diseases.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The term "substantially" is meant to permit deviations from the descriptive term that don't negatively impact the intended purpose. Descriptive terms are implicitly understood to be modified by the word substantially, even if the term is not explicitly modified by the word substantially.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A machine learning system that classifies retinal features and predicts, based on the classified retinal features, an onset or presence of Parkinson's disease (PD) in a human subject, the machine learning system comprising:

a processor configured to perform trained machine learning, wherein one or more trained machine learning models have been trained on stored retinal images obtained from at least a first group of human subjects who have previously been diagnosed as having PD and at least a first group of human subjects who have not previously been diagnosed as having PD, the one or more trained machine learning models performing a process comprising:

receiving a retinal image that has been acquired by an image acquisition system;

processing the acquired retinal image to classify one or more retinal features contained in the acquired retinal image; and predicting, based on the classification, whether the retinal image is indicative of an onset or presence of PD in the human subject; and a memory device in communication with the processor, the memory device storing computer instructions comprising the one or more trained machine learning models for execution by the processor, wherein the one or more trained machine learning models is configured in a pipeline architecture comprising a trained vessel map generator machine learning model in a first stage of the pipeline architecture and a trained PD classifier machine learning model in a second stage of the pipeline architecture that follows the first stage.

2. The machine learning system of claim 1, wherein the retinal images comprise retinal fundus images.

3. The machine learning system of claim 1, wherein during training of the PD classifier machine learning model, the trained vessel map generator machine learning model generates respective vessel maps for each respective retinal image inputted to the first stage and outputs the vessel maps to the second stage.

4. The machine learning system of claim 3, wherein during training of the PD classifier machine learning model, the vessel maps outputted to the second stage are used to train the PD classifier model.

5. The machine learning system of claim 1, wherein after the PD classifier machine learning model has been trained to classify retinal images, a retinal image obtained from a patient is processed by the trained vessel map generator machine learning model to produce a respective vessel map that is outputted to the second stage, and wherein the respective vessel map is processed by the trained PD classifier machine learning model to predict, based on the classification, whether the retinal image is indicative of an onset or presence of PD in the human subject.

6. A method for identification of onset or presence of Parkinson's disease (PD) in a human subject, comprising:

receiving, by processing circuitry, a retinal image that has been acquired by an image acquisition system;

processing, by the processing circuitry, the acquired retinal image using one or more trained machine learning models to classify one or more retinal features contained in the acquired retinal image, wherein the one or more trained machine learning models is configured in a pipeline architecture comprising a trained vessel map generator machine learning model in a first stage of the pipeline architecture and a trained PD classifier machine learning model in a second stage of the pipeline architecture that follows the first stage; and predicting, by the processing circuitry, whether the retinal image is indicative of an onset or presence of PD in the human subject based on the classification.

7. The method of claim 6, wherein the one or more trained machine learning models have been trained on stored retinal images obtained from at least a first group of human subjects who have previously been diagnosed as having PD and at least a first group of human subjects who have not previously been diagnosed as having PD.

8. The method of claim 6, wherein the retinal image is a retinal fundus image.

9. The method of claim 6, wherein the retinal image is generated from an optical coherence tomography (OCT) image.

10. The method of claim 6, comprising training a PD classifier machine learning model to generate the trained PD classifier machine learning model.

11. The method of claim 10, wherein during training of the PD classifier machine learning model, the trained vessel map generator machine learning model generates respective vessel maps for each respective retinal image inputted to the first stage and outputs the vessel maps to the second stage.

12. The method of claim 11, wherein during training of the PD classifier machine learning model, the vessel maps outputted to the second stage are used to train the PD classifier model.

13. The method of claim 10, comprising:

processing a retinal image obtained from a patient by the trained vessel map generator machine learning model to produce a respective vessel map that is outputted to the second stage; and processing the respective vessel map by the trained PD classifier machine learning model to predict, based on the classification, whether the retinal image is indicative of an onset or presence of PD in the human subject.

\* \* \* \* \*